(12) United States Patent
Levin

(10) Patent No.: US 10,682,209 B2
(45) Date of Patent: *Jun. 16, 2020

(54) ESTIMATING A SURFACE TEXTURE OF A TOOTH

(71) Applicant: Align Technology, Inc., San Jose, CA (US)

(72) Inventor: Adi Levin, Nes Tziona (IL)

(73) Assignee: Align Technology, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/282,431

(22) Filed: Feb. 22, 2019

(65) Prior Publication Data

US 2019/0183614 A1    Jun. 20, 2019

Related U.S. Application Data

(63) Continuation of application No. 15/797,959, filed on Oct. 30, 2017, now Pat. No. 10,238,472, which is a
(Continued)

(51) Int. Cl.
*G06K 9/00* (2006.01)
*A61C 9/00* (2006.01)
(Continued)

(52) U.S. Cl.
CPC ........ *A61C 9/0073* (2013.01); *A61B 1/00009* (2013.01); *A61B 1/0607* (2013.01);
(Continued)

(58) Field of Classification Search
CPC ........... A61B 1/00009; A61B 1/00096; A61B 1/0615; A61B 1/0638; A61B 1/0646;
(Continued)

(56) References Cited

U.S. PATENT DOCUMENTS

| 6,201,880 B1 | 3/2001 | Elbaum et al. |
| 7,319,529 B2 | 1/2008 | Babayoff |

(Continued)

FOREIGN PATENT DOCUMENTS

| EP | 2078493 A2 | 7/2009 |
| JP | 09253100 | 9/1997 |

(Continued)

OTHER PUBLICATIONS

University of Illinois."Low-Rank Matrix Recovery and Completion via Convex Optimization: Robust Protometric Stereo via Low-Rank Matrix Completion and Recovery". Retrieved from http://perception.csl.uiuc.edu/matrix-rand/stereo.html, Jun. 4, 2012, 3 pages.

(Continued)

*Primary Examiner* — Tom Y Lu
(74) *Attorney, Agent, or Firm* — Shay Glenn LLP

(57) ABSTRACT

Embodiments for estimating a surface texture of a tooth are described herein. One method embodiment includes collecting a sequence of images utilizing multiple light conditions using an intra-oral imaging device and estimating the surface texture of the tooth based on the sequence of images.

20 Claims, 4 Drawing Sheets

Related U.S. Application Data continuation of application No. 14/921,897, filed on Oct. 23, 2015, now Pat. No. 9,801,698, which is a continuation of application No. 13/631,571, filed on Sep. 28, 2012, now Pat. No. 9,192,305.

(51) Int. Cl.
| | | |
|---|---|---|
| *A61B 5/00* | (2006.01) | |
| *A61B 1/00* | (2006.01) | |
| *A61B 1/06* | (2006.01) | |
| *A61B 1/24* | (2006.01) | |
| *A61C 1/08* | (2006.01) | |

(52) U.S. Cl.
CPC .............. *A61B 1/24* (2013.01); *A61B 5/0088* (2013.01); *A61B 5/4547* (2013.01); *A61C 1/088* (2013.01); *A61C 9/0066* (2013.01)

(58) Field of Classification Search
CPC ....... A61B 1/0676; A61B 1/0684; A61B 1/24; A61B 1/247; A61B 5/0088; A61B 5/1077; A61C 9/0066; G01B 11/24; G01J 3/02; G01J 3/0205; G01J 3/0208; G01J 3/0216; G01J 3/0218; G01J 3/0224; G01J 3/0243; G01J 3/0256; G01J 3/10; G01J 3/462; G01J 3/50; G01J 3/501; G01J 3/508; G01J 3/51; G06T 2207/10024; G06T 2207/10028; G06T 2207/30036; G06T 7/0012; G06T 7/0083; G06T 7/408; H04N 13/0207; H04N 13/0257; H04N 13/0296

See application file for complete search history.

(56) References Cited

U.S. PATENT DOCUMENTS

| | | |
|---|---|---|
| 8,570,530 B2 | 10/2013 | Liang |
| 9,192,305 B2 | 11/2015 | Levin |
| 9,801,698 B2 | 10/2017 | Levin |
| 2002/0150859 A1 | 10/2002 | Imgrund et al. |
| 2005/0003323 A1 | 1/2005 | Katsuda et al. |
| 2008/0021584 A1 | 1/2008 | Whaite et al. |
| 2009/0087050 A1 | 4/2009 | Gandyra |
| 2009/0181339 A1 | 7/2009 | Liang et al. |
| 2010/0189341 A1 | 7/2010 | Oota et al. |
| 2010/0311005 A1 | 12/2010 | Liang |
| 2011/0080576 A1* | 4/2011 | Thiel .................... G01B 11/026 356/73 |
| 2011/0136090 A1* | 6/2011 | Kazemi ................ G09B 23/283 434/263 |
| 2011/0229842 A1 | 9/2011 | Bielfeldt et al. |

FOREIGN PATENT DOCUMENTS

| | | |
|---|---|---|
| JP | 2006187470 | 7/2006 |
| JP | 2007296249 A | 11/2007 |
| JP | 2009078133 A | 4/2009 |
| JP | 2010122158 | 6/2010 |
| JP | 2010194296 A | 9/2010 |
| WO | 2008033218 A1 | 3/2008 |

OTHER PUBLICATIONS

Jerry's Taurus Studio, 3D Surface Texture Analysis—Photometric Stereo—Introduction. Last update: Jun. 2009. Retrieved from http://www.taurusstudio.net/research/photex/ps/index.htm, Jun. 4, 2012, 2 pages.
Logozzo, Silvia , et al. A Comparative Analysis of Intraoral 3d Digital Scanners for Restorative Dentistry. The Internet Journal of Medical Technology. ISSN: 1559-4610. Retrieved from http://www.ispub.com/journal/the-internet-journal-of-medical-technology/volume-5-numb . . . , Jun. 27, 2012, 24 pages.
University of Kentucky. Graphics Vision Technology Laboratory. Gravity at VIS.UKY.EDU. Retrieved from http://vis.usk.edu/~gravity/research.htm, Jun. 7, 2012, 12 pages.
First Examination Report from related Australia Patent Application No. 2013322309, dated Oct. 26, 2016, 4 pages.
International Search Report and Written Opinion from related PCT Application No. PCT/IB2013/002044, dated Feb. 5, 2014, 11 pages.
International Preliminary Report on Patentablility from related PCT Application No. PCT/IB2013/002044, dated Mar. 31, 2015, 7 pages.
Office Action from related Japan Patent Application No. 2015-533707, dated Jun. 20, 2017, 4 pages.
Office Action from related Chinese Application No. 201380062192, dated Jun. 27, 2016, 8 pp.
Decision to Grant from related Japan Patent Application No. 2015533707, dated Mar. 13, 2018, 3 pages.
Final Office Action from related Japanese Application No. 2015-533707 dated Dec. 19, 2017 (3 pages).

* cited by examiner

ESTIMATING A SURFACE TEXTURE OF A TOOTH

PRIORITY INFORMATION

This application is a Continuation of U.S. application Ser. No. 15/797,959, filed Oct. 30, 2017, which is a Continuation of U.S. application Ser. No. 14/921,897 now U.S. Pat. No. 9,801,698, filed Oct. 23, 2015, which is a Continuation of U.S. application Ser. No. 13/631,571, now U.S. Pat. No. 9,192,305, filed Sep. 19, 2014, the entire contents of which are hereby incorporated by reference.

TECHNICAL FIELD

The present disclosure relates to systems and methods for estimating a surface texture of a tooth.

BACKGROUND

The present disclosure is related generally to the field of dental treatment. More particularly, the present disclosure is related to methods, devices, and systems for estimating a surface texture of a tooth.

Dental treatments may involve, for instance, restorative (e.g., prosthodontic) and/or orthodontic procedures. Prosthodontic procedures may be designed to implant a dental prosthesis (e.g., a crown or bridge) in the intra-oral cavity of a patient. Restorative procedures (e.g., other than prosthodontic) may include creating restorations for broken, damaged, or missing teeth, among others. Orthodontic procedures may include repositioning misaligned teeth and changing bite configurations for improved cosmetic appearance and/or dental function. Restorative repositioning can be accomplished, for example, by applying controlled forces to one or more teeth over a period of time.

A scanning system may be used to obtain a digital data representing a patient's teeth in their then current position (e.g., at the time of the scan) which will be considered, as used herein an initial digital data set (IDDS) representing an initial tooth arrangement. The IDDS may be obtained in a variety of ways. This can be used for dental records or treatment purposes.

For example, the patient's teeth may be imaged to obtain digital data using direct and/or indirect structured light, X-rays, three-dimensional X-rays, lasers, destructive scanning, computing device-aided tomographic images or data sets, magnetic resonance images, intra-oral scanning technology, photographic reconstruction, and/or other imaging techniques. The IDDS can include an entire mouth tooth arrangement, some, but not all teeth in the mouth, and/or it can include a single tooth.

DETAILED DESCRIPTION

Figure 1A:
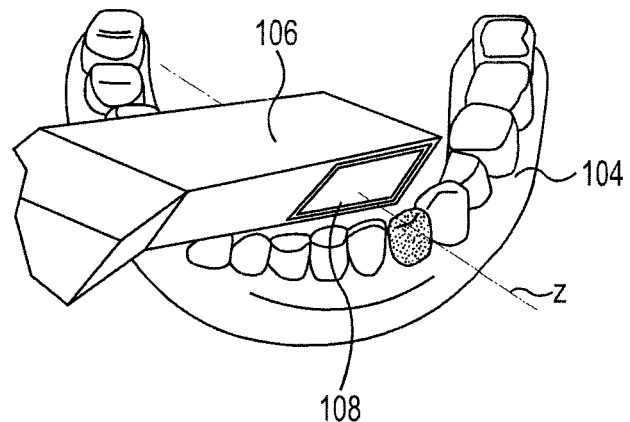
FIGS. 1A-1D illustrate alternative views of a dental device according to a number of embodiments of the present disclosure
Figure 1B:
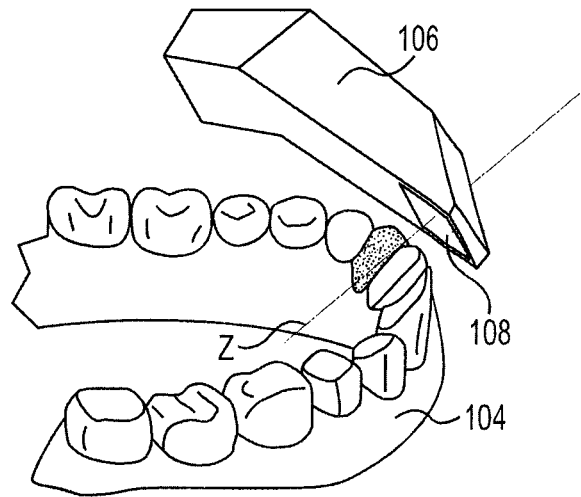
Figure 1C:
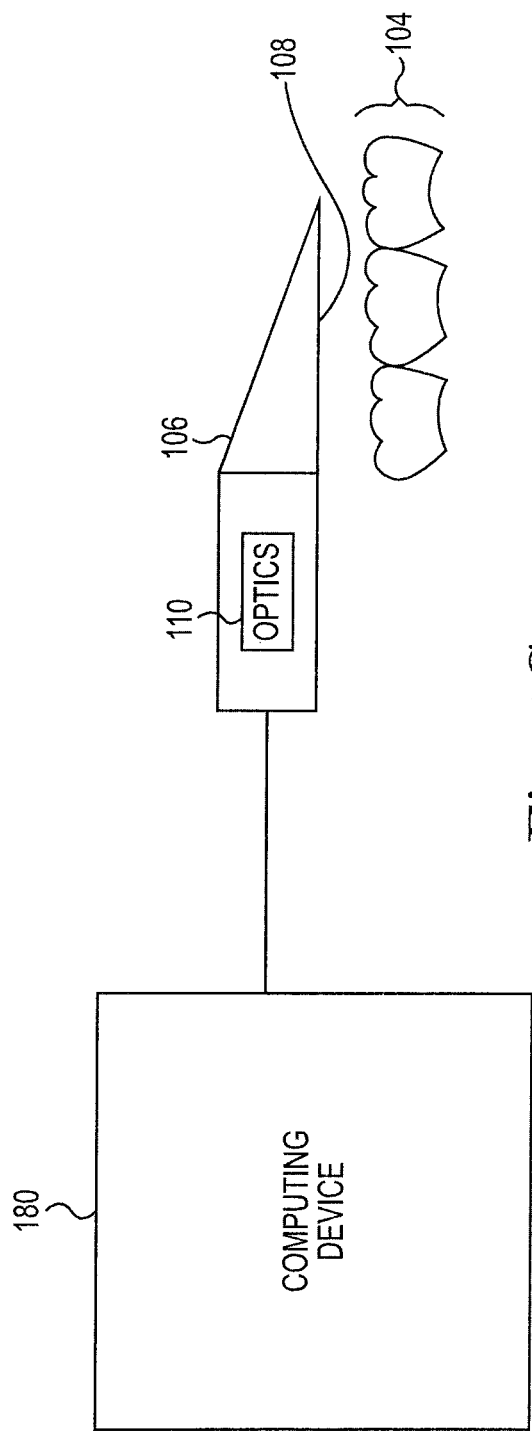
Figure 1D:
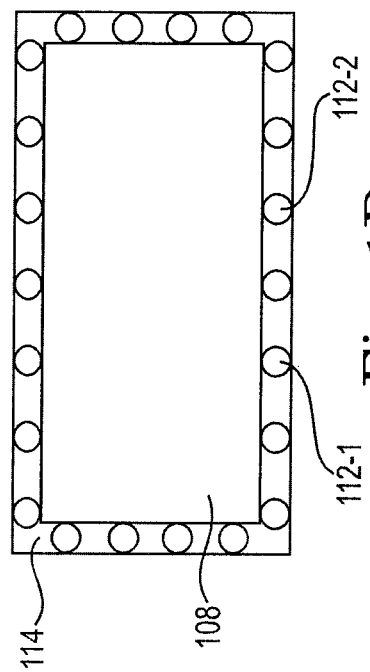

A positive model and/or negative impression of the patient's teeth or a tooth may be scanned, for example, using an X-ray, laser scanner, destructive scanner, structured light, and/or other range acquisition system to produce the IDDS. The data set produced by the range acquisition system may be converted to other formats to be compatible with the software which is used for collecting images within the data set, and estimating surface texture of a tooth, as described herein.

Whether scanning a patient's dentition directly, or scanning a model or impression of the patent's dentition, it may be desirable to support scanning that can capture surface texture of a tooth. Such support can be beneficial for both video scanning (e.g., a continuous sequence of images) and point-and-shoot scanning (e.g., a number of discrete images). Unless otherwise noted, the term scan, as used herein, can refer to either or both of video and point-and-shoot scanning.

Some difficulties may arise with scanning when capturing fine three-dimensional (3D) detail of teeth texture is desired. Rather than capturing fine detail of tooth texture, the use of a dental device (e.g., optical device, intra-oral device, etc.) can result in capturing an overall shape of a tooth, which can lack information needed by a dental technician to produce a natural-looking dental restoration, for example. Without a surface texture of a tooth, (e.g., changes in surface "heights" of a tooth) a dental technician may lose a significant amount of information about the tooth's appearance.

The present disclosure provides computing device implemented methods, computing device readable media, and systems for estimating a surface texture of a tooth. Estimating a surface texture of a tooth can include collecting a sequence of images utilizing multiple light conditions using an intra-oral imaging device and estimating the surface texture of the tooth based on the sequence of images.

In some embodiments, a dental device can include an array of individual light sources, each individual light source capable of being turned on and off independently and an optics device capable of capturing an image of a number of teeth. In some embodiments, a first image of one of the number of teeth can be captured using a first individual light source, and a second image of the one of the number of teeth can be captured using a second individual light source.

In a number of embodiments, estimating a surface texture of a tooth can include receiving a sequence of scanned images of a tooth from a dental scanner, the sequence including a number of individual images, each individual image scanned under a different light condition. Estimating a surface texture of a tooth can also include comparing at least two of the individual images within the sequence to one another and estimating the surface texture of the tooth based on the comparison. In some examples, differences between pixel intensities in different individual images can be compared, and the comparison can be used to estimate the tooth texture.

In the detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure. As used herein, the designator "N", particularly with respect to reference numerals in the drawings, indicates that a number of the particular feature so designated can be included. As used herein, "a number of" a particular thing can refer to one or more of such things (e.g., a number of teeth can refer to one or more teeth).

The figures herein follow a numbering convention in which the first digit or digits correspond to the drawing figure number and the remaining digits identify an element or component in the drawing. Similar elements or components between different figures may be identified by the use of similar digits. For example, 106 may reference element "06" in FIG. 1, and a similar element may be referenced as 306 in FIG. 3. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

FIGS. 1A-1D illustrate alternate views of a dental device (e.g., an intra-oral scanner) according to a number of embodiments of the present disclosure. In some examples, device 106 can include a 3D scanner, and/or a 3D scanner in combination with a two dimensional imager. The spatial relationship of the device 106 with respect to a dentition 104 in the intra-oral cavity is shown. A plurality of images showing the relationship at any other desired vantage point (viewpoint) may be provided on a display, including for example the vantage point as would be seen by a dental practitioner with respect to a real intra-oral cavity, either by default or by being chosen by the user by interacting with a computing device (e.g., computing device 180 shown in FIG. 10) controlling the device 106. A dynamic image can be provided, in which the user can change the vantage point of the image interactively. A video clip or the like may be provided for providing the user with a sequence of operations of the scanner.

Images presented on a display to a user can be composites of virtual models of the dentition 104 as created with aid of the device 106 and stored in memory. These virtual models can be manipulated by the user and/or the computing device to provide the correct spatial relationship, in virtual space and can be displayed as 2D or 3D images. Optionally, the position of the device 106 and the direction of the scanning axis (e.g., z-axis) can be displayed with respect to the dentition 104. The scanning axis (e.g., z-axis) can be defined as orthogonal to the scanning face 108 of the device 106, but may be defined according to other suitable geometric or other parameters of the scanner 106. The images of the dentition 104 can be displayed as having 3D attributes and realistic dental morphologies and/or each dental surface can be represented, for example, by a geometrical form (e.g., simple wedges representing incisors, cones representing canines, and cylinders representing molars).

The virtual model can be custom-modified to show a virtual preparation at each corresponding dental site where a real preparation is to be found, and also virtual teeth may be removed from the model where none are to be found in the real intra-oral cavity (e.g., where teeth have been removed for accommodating a pontic). These features can further facilitate identification of the positions and orientations of the device 106 with respect to the dentition 104.

Non-image data can be provided identifying the position and orientation of the device 106 with respect to the dentition 104 (e.g., the relationships), and this data may be provided, for example, in the form of a table listing suitable corresponding geometric data, and also including, for example, the spacing between the scanning face 108 and the dental surface of interest, an identification of the particular surface being scanned, etc. The relationships can be displayed in alphanumeric form, as a set of instructions or statements describing the relative positions of the device 106 and the dentition 104, for example. The relationships can be displayed in audible form, wherein for example such instructions or statements are broadcast by a speaker or the like, either from a prerecording, or synthetically created by the computing device.

Figure 3:
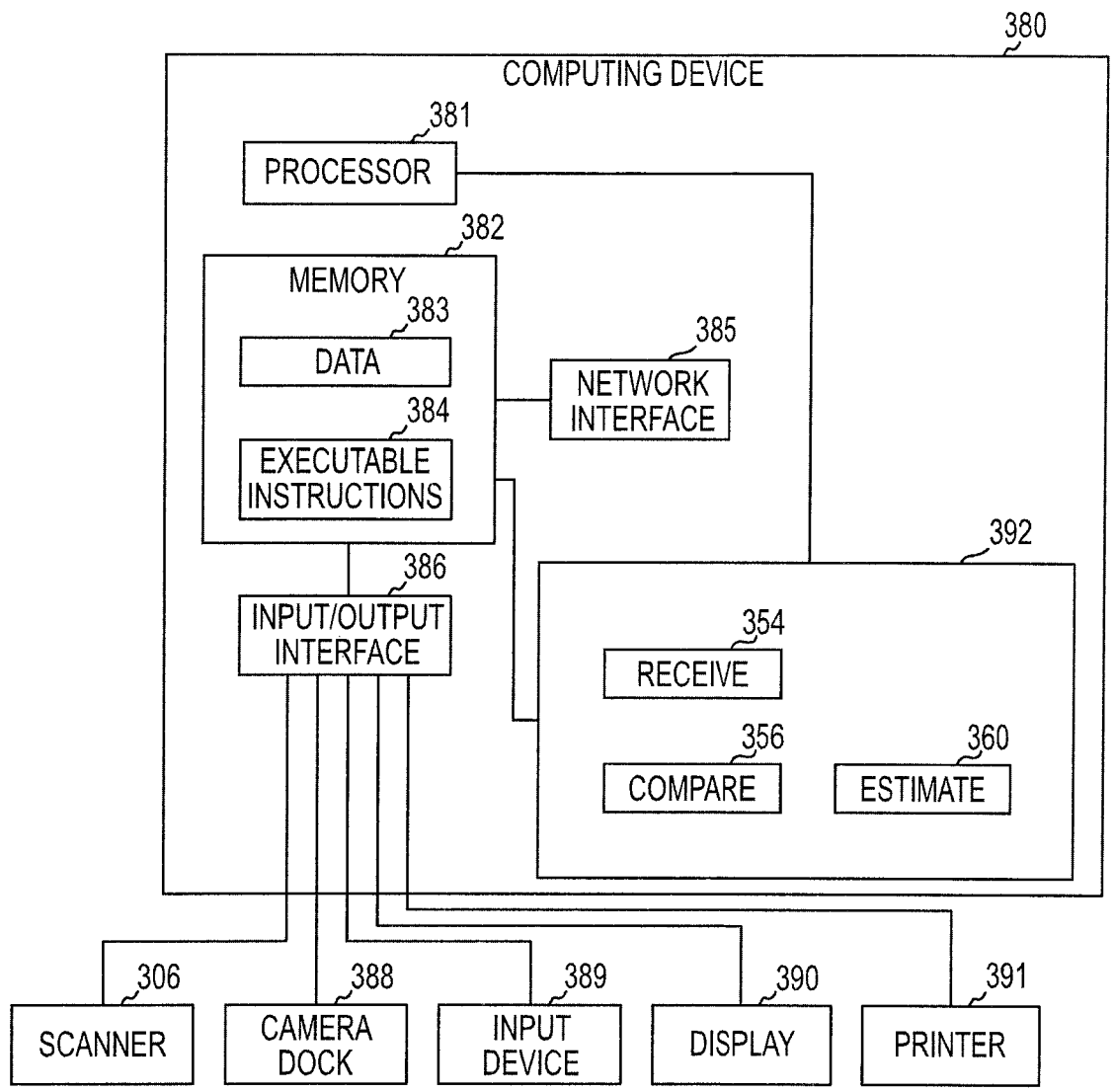
FIG. 3 illustrates a system for estimating a surface texture of a tooth according to a number of embodiments of the present disclosure.

Device 106 can include an optics device 110 capable of capturing an image of a number of teeth of dentition 104, for example. In a number of embodiments, optics device 110 can be included as a part of device 106, within computing device 180, or can be a separate component. Optics device 110 can, for example, capture an entire image with increased focus over a variety of 3D imaging, including, for example, confocal imaging. In some embodiments, device 106, optics device 110, and/or computing device 180 can include a database (e.g., memory 382, as illustrated in FIG. 3) in which to store a captured image.

Scanning face 108 can include an array 114 of individual light sources (e.g., light sources 112-1 and 112-2). In a number of embodiments, a light source may not include an original light source (e.g., one light source can power a number of illumination sites) and/or a light source can include a number of lights from a single source. A light source, for example, can be a local light source with respect to an image. In some embodiments, a light source can include a remote original light source and/or an illumination site that can be moved (e.g., via a mirror) to have an effect of light moving or coming from a number of directions.

In a number of examples, a light source can include one or more illumination sites which illuminate an object (e.g., at one point in time). Each illumination site can be its own original source of illumination, and/or it can be remotely illuminated from one or more original light sources (e.g., via a mirror, fiber optics, etc.). In some examples, an additional light source can include one or more illumination sites where one or more of the illumination sites is different (e.g., location, frequency, etc.) from an original light source relative to an object being illuminated.

In some examples, device 106 can focus the individual light sources of array 114 to determine a structure, texture, slope, orientation, etc. of a tooth. Any number of individual light sources may be used within array 114. The individual light sources can include a number of different shapes and/or types of light sources, such as, for example, light-emitting diode (LED) light sources, halogen light sources, xenon light sources, etc. In some embodiments, the individual light sources can include, for example, fiber optics on, in, and/or attached to the device 106. A different light source can be used, for example, to power the fiber optics, utilizing optical switches to turn all or a portion of the fiber optics on and/or off. In a number of embodiments, each of the individual light sources can be capable of being turned on and off independently or in any combination.

In a number of embodiments, array 114 of individual light sources can include individual light sources in the form of a ring, however, embodiments are not limited to a ring formation. For example, array 114 can include individual light sources in alternating positions and patterns. In some embodiments, the individual light sources can be moveable, include a moveable mirror, and/or include a moveable light support structure (e.g., on scanning face 108), for example. Array 114 can include, for example, two or more different light locations relative to an object, which can be from one original light source (e.g., using a moveable mirror and/or fiber optics) and/or can be from multiple original light sources. In some examples, a same light source can be used as the source used for the scanner when fiber optics are utilized.

Array 114 can be detachable from device 106 in some examples, and can be retrofit onto an existing device (e.g., intra-oral scanner) in some embodiments. For example, array 106 can be an attachment at a tip of and existing device and/or device 106, to be used in areas where identification of surface texture is desired (e.g., anterior teeth). In other embodiments, array 114 is not detachable, but a fixed part of device 106. In some embodiments, device 106 can be detachable from a different dental device used in intra-oral scanning, for example.

In a number of embodiments, array 114 can be located at an end of device 106 and/or can be located substantially near an end of device 106, for example. An array at an end of device 106 can be included in any of: a device including an array of individual light sources comprised of one or more illumination sites, each individual light source capable of being turned on and off independently and an optics device capable of capturing an image of a number of teeth, wherein a first image of one of the number of teeth is captured using a first individual light source, and a second image of the one of the number of teeth is captured using a second individual light source; the device including a database in which to store the captured images; and/or the array of individual light sources includes individual light-emitting diode (LED) light sources, halogen light sources, and/or xenon light sources, among others.

In an example, an array located substantially near an end of device 106 can be included in any of: a device including an array of individual light sources comprised of one or more illumination sites, each individual light source capable of being turned on and off independently and an optics device capable of capturing an image of a number of teeth, wherein a first image of one of the number of teeth is captured using a first individual light source, and a second image of the one of the number of teeth is captured using a second individual light source; the device including a database in which to store the captured images; and/or the array of individual light sources includes individual light-emitting diode (LED) light sources, halogen light sources, and/or xenon light sources, among others.

In a number of embodiments, a detachable array can be included in any of: a device including an array of individual light sources, each individual light source capable of being turned on and off independently and an optics device capable of capturing an image of a number of teeth, wherein a first image of one of the number of teeth is captured using a first individual light source, and a second image of the one of the number of teeth is captured using a second individual light source; the device including a database in which to store the captured images; and/or the array of individual light sources includes individual light-emitting diode (LED) light sources. For example, in any of the above-described embodiments, the individual light sources can be detachable.

In some examples, an array in the form of a ring can be included in any of: a device including an array of light sources, each individual light source including one or more illumination sites capable of being turned on and off independently and an optics device capable of capturing an image of a number of teeth, wherein a first image of one of the number of teeth is captured using a first individual light source, and a second image of the one of the number of teeth is captured using a second individual light source; the device including a database in which to store the captured images; and/or the array of individual light sources includes individual light-emitting diode (LED) light sources, halogen light sources, and/or xenon light sources, among others. For example, in any of the above-described embodiments, the array can be in the form of a ring.

Images can be captured by device 106 using different individual light sources, in some embodiments. For example, an image of a tooth can be captured with optics device 110 using individual light source 112-1, and a different image of the tooth can be captured using individual light source 112-2. These different images can be used to estimate a surface texture of the tooth, for example.

In a number of embodiments, a dental device for estimating tooth texture can be separate from an intra-oral scanner and can include a camera and a number of light sources, for example.

Figure 2:
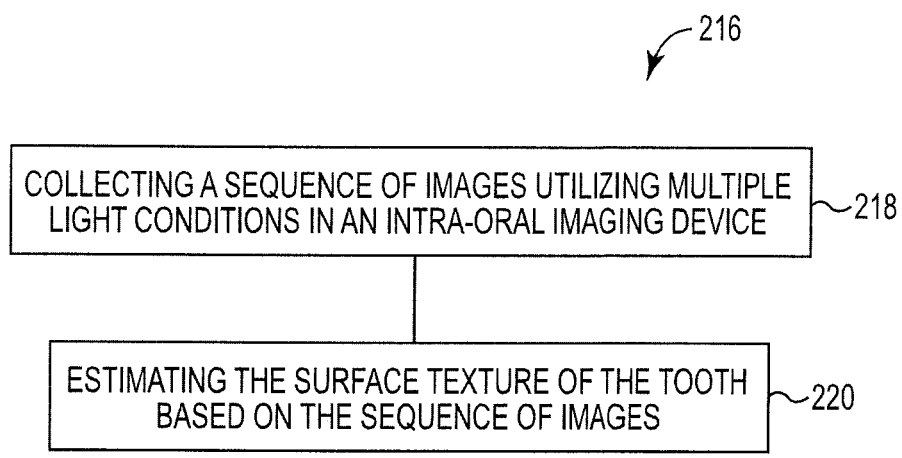
FIG. 2 is a flow chart illustrating an example of a method for estimating a texture of a tooth according to a number of embodiments of the present disclosure.

FIG. 2 is a flow chart illustrating an example of a method 216 for estimating a surface texture of a tooth according to one or more embodiments of the present disclosure. Enhancing details in a 3D image of a tooth by capturing reflectance of light in a way that is increasingly sensitive to small changes in the surface texture of the a tooth can result in more accurate representative images (e.g., images of tooth texture) of a tooth, for example. These representative images can be used in some embodiments to create or produce tooth restorations (e.g., veneers).

At 218, a sequence of images is collected utilizing multiple light conditions using an intra-oral imaging device. In a number of embodiments, a dental device, such as device 106 can be the intra-oral imaging device used to collect (e.g., capture) the sequence of images. The sequence of images can be collected individually, and in some embodiments, a different light source can be used to collect each image with the sequence. Collecting the sequence of images under multiple light conditions (e.g., multiple varying light conditions and/or sources) can create and/or enhance an illusion of depth in an image, for example.

For example, a first individual light source can be turned on, a first image can be collected, and the first individual light source can be turned off. A second individual light source can be turned on, and a second image can be collected. The second individual light source can be turned off. This process can be repeated for any number of light sources, light source combinations, and/or images. In a number of embodiments, the lights can be turned on and off at the same or varying lengths of time and/or increments, for example.

Collecting the sequence of images can include, for example, collecting a sequence of images of the same area of the same tooth under multiple light conditions. In some embodiments a portion of a particular tooth may be a focal point, so a sequence of images of just that portion can be collected, for example.

In a number of embodiments, the multiple light conditions can include a different number of light sources such as, for example, a different combination of light sources, a number of light sources from a number of different directions and/or locations, a number of light sources of different frequencies, a number of light sources on different spectrums, and/or a number of light sources of different intensities, among others.

The sequence of images can also be collected using a moving light source, for example. The light source can be moved along a path (e.g., a particular, predetermined path) and/or a number of different paths while continuously collecting images. In some examples, this can have a same or similar effect as turning individual light sources on and off.

In a number of embodiments, collecting a sequence of images of approximately the same area of the same tooth under multiple light conditions can be included in any of: a method for estimating a surface texture of a tooth that includes collecting a sequence of images utilizing multiple light conditions (e.g., a different number of light sources, a different combination of light sources, a number of light sources from different directions and/or locations, a number of light sources of different frequencies, a number of light sources on different spectrums, a moving light source, and a number of light sources of different intensities) using an intra-oral imaging device and estimating the surface texture of the tooth based on the sequence of images; the method, wherein collecting the sequence of images utilizing multiple light conditions includes utilizing a different light source to capture each image within the sequence; the method, including comparing the collected sequence of images to a dental model of the tooth; the method, wherein comparing the collected sequence of images includes converting the collected sequence of images to normal vector information per pixel of each of the images within the sequence; and/or the method, wherein comparing the collected sequence of images includes automatically computing. For example, in any of the above-described embodiments, a sequence of images of approximately the same area of the same tooth under multiple light conditions can be collected.

In some examples, collecting a sequence of images using a dental device that includes a ring of light sources comprised of one or more illumination sites can be included in any of: a method for estimating a surface texture of a tooth that includes collecting a sequence of images utilizing multiple light conditions (e.g., having a different number of light sources such as a different combination of light sources, a number of light sources from different directions and/or locations, a number of light sources of different frequencies, a number of light sources on different spectrums, a moving light source, and a number of light sources of different intensities) using an intra-oral imaging device and estimating the surface texture of the tooth based on the sequence of images; the method, wherein collecting the sequence of images utilizing multiple light conditions includes utilizing a different light source to capture each image within the sequence; the method, including comparing the collected sequence of images to a dental model of the tooth; the method, wherein comparing the collected sequence of images includes converting the collected sequence of images to normal vector information per pixel of each of the images within the sequence; and/or the method, wherein comparing the collected sequence of images includes automatically computing. For example, in any of the above-described embodiments, a sequence of images can be collected using a dental device that includes a ring of light sources comprised of one or more illumination sites.

The ring of light sources can be of any shape or size which can affect different light conditions on the object. For example, the ring can be generally circular, oval, straight sided, continuous or discontinuous, FIG. 1D, as but an example, shows one embodiment of the ring to be straight sided of a rectangular shape.

At 220, the surface texture of the tooth is estimated based on the sequence of images. In a number of embodiments, the sequence of images can be images taken of a same area or surface at a same viewpoint under the multiple light conditions. Surface texture can include, for example, changes (e.g., small changes) in a depth of the tooth's surface.

Surface texture can also include, for example, a surface gradient (e.g., slope) of a tooth, surface orientation, and/or an orientation of a tooth.

The collected sequence of images can be compared to a dental model of the tooth in some embodiments. For example, a model and/or restoration previously constructed can be compared to the sequence of images to determine accuracy and realism of the model and/or restoration. In some embodiments, a 3D alignment between the collected sequence of images and the dental model can be automatically computed. For example, a dental model (e.g., 3D dental model) can be scanned, and this scan data can be compared to the collected sequence of images to see if the textures align. In some embodiments, a 3D alignment can be computed (e.g., automatically) between each individual image and the 3D model.

In some examples, computing a 3D alignment between an individual image and a 3D model can be included in any of: receiving a sequence of scanned images of a tooth from a dental device, the sequence including a number of individual images, each individual image collected under a different light condition, comparing at least two of the individual images within the sequence to one another, and estimating the surface texture of the tooth based on the comparison; estimating a surface texture of a neighboring tooth based on the estimated surface texture of the tooth; converting the estimated surface texture of the tooth into a surface normal vector for each pixel of each individual image; and/or adding a detail to the three-dimensional dental model based on the surface normal vector.

In a number of embodiments, the collected sequence of images (e.g., image data) can be converted to normal vector information per pixel of each of the images within the sequence, and the normal vector information can be compared to the dental model. The normal vector can include a vector perpendicular to a surface at a particular point. For example, each pixel of each image can be identified and analyzed individually. A computational model (e.g., algorithm) can be utilized to convert the image data into the normal vector information per pixel of each image. In some examples, a least-squares method can be utilized. For example, the conversion can be made by inverting a linear equation:

$$l = n \times L,$$

where l is a (known) vector of m observed intensities, n is the (unknown) surface normal (e.g., normal vector information), and L is a (known) 3×m matrix of normalized light directions under an assumption of Lambertian reflectance. In some embodiments, a surface texture is estimated and displayed (e.g., via a user interface), and the estimated surface texture is not compared to the dental model.

In some embodiments, dental detail can be added to a dental model (e.g., restoration) based on the estimated surface texture. Dental detail can also be added to a dental model utilizing the per-pixel vector information, for example. The estimated surface texture of the tooth can be converted into a surface normal vector for each pixel of each individual collected image in a number of embodiments. Detail can be added to a 3D model based on the surface normal vector. A surface normal vector can provide increased surface texture over depth measurements alone, for example. In some embodiments, the estimation, normal vector, and per-pixel vector information can be used to determine where on a tooth particular textures should be added for detail, for example.

In some examples, adding dental detail to a dental model based on the estimated surface texture can be included in any of: a method for estimating a surface texture of a tooth that includes collecting a sequence of images utilizing multiple light conditions (e.g., having a different number of light sources such as a different combination of light sources, a number of light sources from different directions and/or locations, a number of light sources of different frequencies, a number of light sources on different spectrums, a moving light source, and a number of light sources of different intensities) using an intra-oral imaging device and estimating the surface texture of the tooth based on the sequence of images; the method, wherein collecting the sequence of images utilizing multiple light conditions includes utilizing a different light source to capture each image within the sequence; the method, including comparing the collected sequence of images to a dental model of the tooth; the method, wherein comparing the collected sequence of images includes converting the collected sequence of images to normal vector information per pixel of each of the images within the sequence; and/or the method, wherein comparing the collected sequence of images includes automatically computing. For example, in any of the above-described embodiments, dental detail to a dental model can be added based on the estimated surface texture.

Surface texture of a tooth can be displayed, for example, by showing a video and/or other illustration of the sequence of images captured under varying light conditions, without aligning them to a 3D model. Surface texture can also be displayed, for example, by aligning the sequence of images to the 3D model, and displaying the image as an overlay over the 3D model, without computing normal vectors from those images.

In a number of embodiments, a surface texture of a neighboring tooth can be estimated based on the estimated surface texture of the tooth. Neighboring teeth can include complimentary tooth textures, and a texture of a tooth that neighbors a different tooth with a known texture may be estimated, based on the known texture, for example. In some embodiments, capturing a surface texture of a neighboring tooth can be used during creation of a veneer restoration for an impaired tooth. For example, the restoration can be designed so that the appearance of the two teeth side-by-side is aesthetically pleasing.

FIG. 3 illustrates a system for estimating a surface texture of a tooth according to a number of embodiments of the present disclosure. The system illustrated in FIG. 3 can include a computing device 380 having a number of components coupled thereto. The computing device 380 can include a processor 381 and memory 382. The memory 382 can include various types of information including data 383 and executable instructions 384 as discussed herein. In a number of embodiments, memory can be divided between a mother-board and a graphic processing unit (GPU), for example.

In some examples of the present disclosure, a system for estimating a surface texture of a tooth can include a number of processing units, and in some embodiments, can include a number of processing units of different kinds. For example, the system can include a field-programmable gate array (FPGA and/or a digital signal processor (DSP) on a chip and/or inside a device (e.g., device 106).

In a number of embodiments, the system can include a GPU to perform a portion of data processing and/or perform graphic computations, for example. The system can also include, for example, a number of processors on computing device 380.

The memory 382 and/or the processor 381 may be located on the computing device 380 or off the device in some embodiments. As such, as illustrated in the embodiment of FIG. 3, a system can include a network interface 385. Such an interface can allow for processing on another networked computing device or such devices can be used to obtain information about the patient or executable instructions for use with various embodiments provided herein.

In a number of embodiments, captured images can be processed inside a dental device (e.g., device 206, 306) in a dedicated computing unit (not pictured), and information collected under varying light conditions (e.g., resulting surface normal vector information) can be transmitted directly from the dental device to a computing device (e.g., computing device 280, 380).

As illustrated in the embodiment of FIG. 3, a system can include one or more input and/or output interfaces 386. Such interfaces can be used to connect the computing device 380 with one or more input or output devices.

For example, in the embodiment illustrated in FIG. 3, the system includes connectivity to a dental device and/or scanner 306 (e.g., an intra-oral scanner including one or more of a 3D scanner and a 2D imager as described herein), a camera dock 388, an input device 389 (e.g., a keyboard, mouse, etc.), a display device 390 (e.g., a monitor), and a printer 391. The input/output interface 386 can receive data, storable in the data storage device (e.g., memory 382), representing 3D and/or 2D data, among other data, corresponding to the patient's dentition. Although the scanner 306 is illustrated as a component separate from computing device 380, in some embodiments, the scanner (e.g., the intraoral scanner) can include the components and/or functionality described herein with respect to the computing device 380.

In some embodiments, the scanner 306 can be configured to scan a physical mold of a patient's upper jaw and a physical mold of a patient's lower jaw. In one or more embodiments, the scanner 306 can be configured to scan the patient's upper and/or lower jaws directly (e.g., intra-orally).

The camera dock 388 can receive an input from an imaging device (e.g., a 2D imaging device) such as a digital camera or a printed photograph scanner separate from any 2D imaging device on the scanner 306. The input from the imaging device can be stored in the data storage device 382.

The processor 381 can be configured to provide a visual indication of a virtual dental model 351 on the display 390 (e.g., on a GUI running on the processor 381 and visible on the display 390). The processor 381 can further be configured (e.g., via computer executable instructions stored in a tangible non-transitory computer readable medium) to perform the various methods, algorithms, and/or functionality described herein. The processor 381, in association with the data storage device 382, can be associated with data and/or application modules 392. The processor 381, in association with the data storage device 382, can store and/or utilize data and/or execute instructions to provide a number of application modules for motion compensation in a 3D scan.

Such connectivity can allow for the input and/or output of virtual dental model information or instructions (e.g., input via keyboard) among other types of information. Although some embodiments may be distributed among various computing devices within one or more networks, such systems as illustrated in FIG. 3 can be beneficial in allowing for the capture, calculation, and/or analysis of information discussed herein.

A system for estimating a surface texture of a tooth can include a scanning module and a processing module (e.g., processor 381). The scanning module can include a dental device (e.g., an intra-oral 3D scanner). The processing module (e.g., processor 381) can (e.g., via application module 392) receive 354 a sequence of scanned images of a tooth from a dental device, the sequence including a number of individual images, each individual image collected under a different light condition. The processing module (e.g., processor 381) can (e.g., via application module 392) compare 356 at least two of the individual images within the sequence to one another, and estimate 360 the surface texture of the tooth based on the comparison. In a number of embodiments, the at least two of the individual images can include 2D images, 3D images, and/or a combination of 2D and 3D images.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A computing device implemented method for estimating a surface texture of a tooth, comprising:

collecting a sequence of images utilizing multiple light conditions and capturing different light intensities using an intra-oral imaging device;

comparing a portion of a first image of the sequence of images captured at a first light intensity to a portion of a second image of the sequence of images captured at a second different light intensity;

estimating the surface texture of the tooth based on the comparison of the first and second different light intensities of the first and second images; and converting the estimated surface texture of the tooth into a surface normal vector for each pixel of at least one of the first and second images.

2. The method of claim 1, wherein the method further includes:

turning different light sources on and off to move an illumination site of the different light sources while collecting the sequence of images.

3. The method of claim 2, wherein the different light sources include at least one of: a different number of light sources, a different combination of light sources, a number of light sources from different directions or locations, a number of light sources of different frequencies, a number of light sources on different spectrums, a moving light source, and a number of light sources of different intensities.

4. The method of claim 2, wherein the different light sources include at least one of: light-emitting diode (LED) light sources, halogen light sources, and xenon light sources.

5. The method of claim 1, wherein the method further includes:

turning different light sources on and off independently to move an illumination site of the different light sources while collecting the sequence of images.

6. The method of claim 1, wherein the method further includes:

turning different light sources on and off to move an illumination site of the different light sources from at least a first position to a second position while collecting the sequence of images.

7. The method of claim 1, wherein the multiple light conditions include light generated from a first combination of light sources to create a first light condition and a second, different combination of light sources to generate a second light condition.

8. The method of claim 1, wherein collecting the sequence of images utilizing multiple light conditions includes utilizing a different light source to capture each image within the sequence.

9. The method of claim 1, wherein the method includes comparing the collected sequence of images to a dental model of the tooth.

10. The method of claim 9, wherein the method includes comparing the normal vector information to a dental model of the tooth.

11. The method of claim 1, wherein the method further includes:

adding a dental detail to a dental model of the tooth based on the surface normal vector.

12. The method of claim 1, wherein comparing the collected sequence of images includes automatically computing a three-dimensional alignment between the sequence of images and a dental model.

13. A non-transitory computing device readable medium having executable instructions that can be executed by a processor to cause a computing device to perform a method for estimating a surface texture of a tooth, comprising:

receiving a sequence of scanned images of a tooth from a dental device, the sequence including a number of individual images, each individual image collected under a different light condition, wherein the different light condition includes capturing different light intensities from multiple sources in each individual image;

comparing a portion of a first image of the sequence of images captured at a first light intensity to a portion of a second image of the sequence of images captured at a second different light intensity;

estimating the surface texture of the tooth based on the comparison of the first and second different light intensities of the first and second images; and converting the estimated surface texture of the tooth into a surface normal vector for each pixel of at least one of the first and second images.

14. The medium of claim 13, wherein the instructions are further executable to compute a three-dimensional alignment between each individual image and a three-dimensional dental model.

15. The medium of claim 13, wherein estimating the surface texture of the tooth includes a surface gradient of the tooth.

16. The medium of claim 13, wherein the method further includes estimating a surface texture of a neighboring tooth, based on the estimated surface texture of the tooth.

17. The medium of claim 13, wherein estimating the surface texture of the tooth includes estimating the surface texture of the tooth based on the comparison of the light intensities from the at least two individual images within the sequence of images.

18. The medium of claim 13, wherein estimating the surface texture of the tooth includes estimating the surface texture of the tooth based on the comparison of the pixel intensities from the at least two individual images within the sequence of images.

19. The medium of claim 13, wherein the method further includes adding a dental detail to a dental model based on the surface normal vector.

20. The medium of claim 13, wherein the dental device, comprises:

an array of individual light sources, each individual light source capable of being turned on and off independently to move an illumination site of the array of individual light sources along a path;

an optics device capable of capturing an image of a number of teeth,
   wherein a first image of one of the number of teeth is captured using a first individual light source, and a second image of the one of the number of teeth is captured using a second individual light source; and a database capable of storing the captured images.

* * * * *